United States Patent [19]

Kaartinen

[11] Patent Number: 5,311,896
[45] Date of Patent: May 17, 1994

[54] METHOD FOR PRODUCING A HEATABLE AND REFRIGERABLE ELEMENT FOR A SYSTEM HANDLING SMALL QUANTITIES OF LIQUID, AND AN ELEMENT MANUFACTURED BY THE METHOD

[76] Inventor: Niilo Kaartinen, Vuolahti, SF-21620 Kuusisto, Finland

[21] Appl. No.: 768,654
[22] PCT Filed: Apr. 10, 1990
[86] PCT No.: PCT/FI90/00102
 § 371 Date: Oct. 7, 1991
 § 102(e) Date: Oct. 7, 1991
[87] PCT Pub. No.: WO90/12350
 PCT Pub. Date: Oct. 18, 1990

[30] Foreign Application Priority Data
 Apr. 10, 1989 [FI] Finland .................. 891697

[51] Int. Cl.5 .................. F16L 55/18; F15C 1/04
[52] U.S. Cl. .................. 137/15; 137/828; 137/315; 205/73; 346/140 R
[58] Field of Search .................. 204/9; 346/140 R; 137/828, 315, 15; 205/73

[56] References Cited
U.S. PATENT DOCUMENTS
4,012,293 3/1977 Meyerhoff .................. 204/9
4,255,237 3/1981 Obert et al. .................. 204/9
4,285,779 8/1981 Shiga et al. .................. 204/9
4,651,174 3/1987 Bava et al. .................. 346/140

FOREIGN PATENT DOCUMENTS
57850 6/1980 Finland .
70331 2/1986 Finland .
2189746 4/1987 United Kingdom .

Primary Examiner—A. Michael Chambers
Attorney, Agent, or Firm—Klarquist, Sparkman, Campbell, Leigh & Whinston

[57] ABSTRACT

The invention relates to a method for producing a heatable and refrigerable element (12) for a system handling small amounts of liquid and to an element manufactured by the method. The element comprises flow channels (11) and one or more liquid spaces (8) communicating with them, the channels being provided with valves (10) connected to a refrigerator (25) and a heater (18), for blocking the channels by freezing the liquid in them. The element (12) is produced by using a removable mould which serves as a substrate for deposition and by depositing one or more metallic materials by electroformation or an equivalent procedure in such a way that the deposited metal forms a shell (5, 7) by removing the mould from inside the shell by dissolving or smelting, and by connecting the shell at the spot of the valves to a refrigerator (25) and a heater (18). The deposition is carried out so that there is a higher thermal conductivity at the spot of the valves (10) than in the adjacent shell areas.

39 Claims, 4 Drawing Sheets

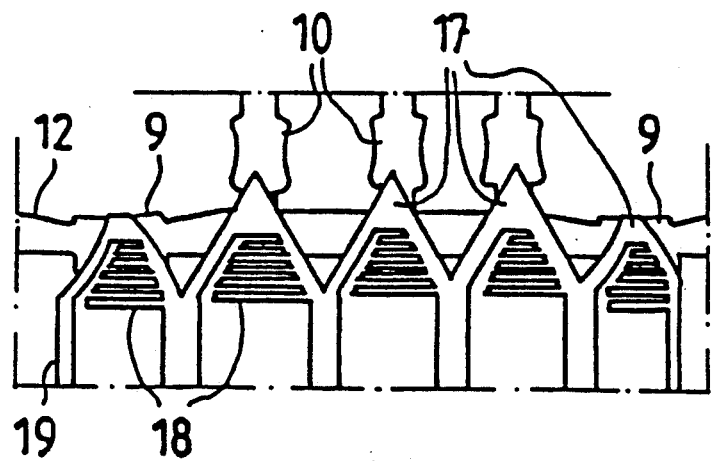
Fig. 9
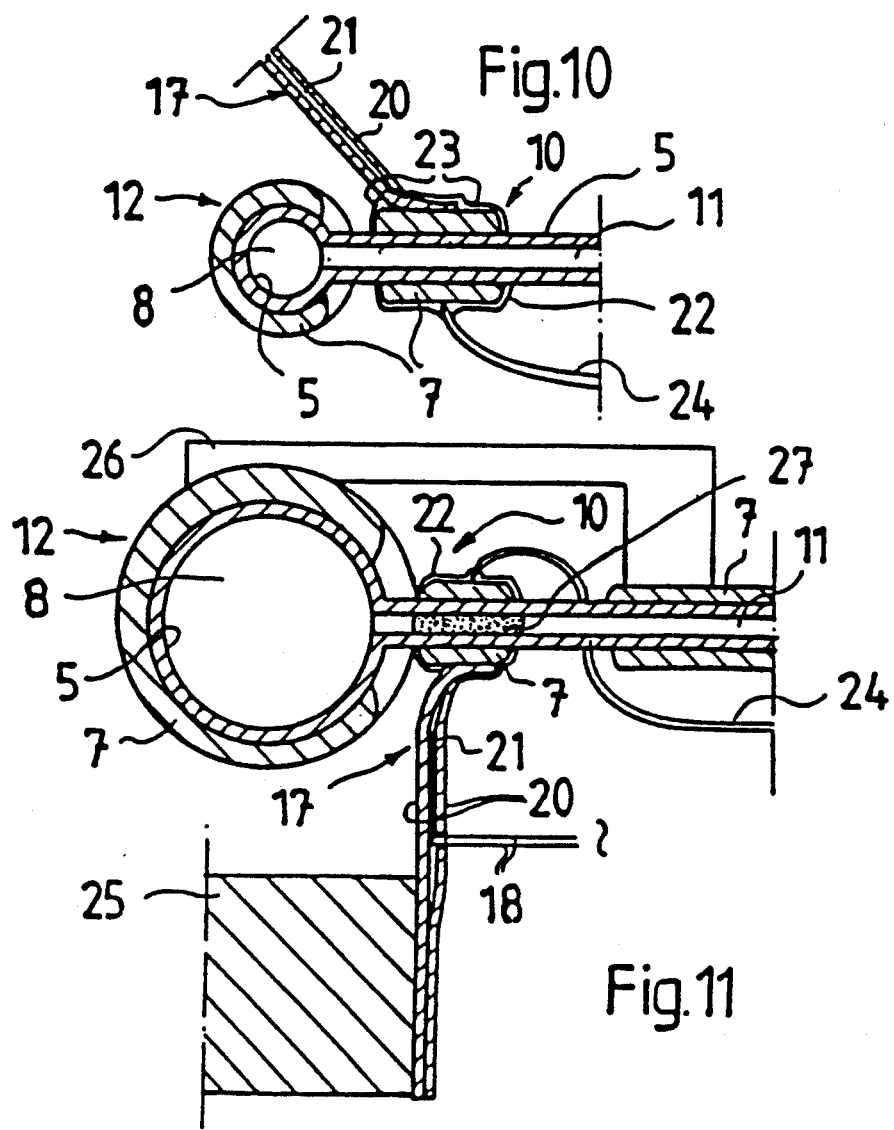
Fig. 10
Fig. 11

METHOD FOR PRODUCING A HEATABLE AND REFRIGERABLE ELEMENT FOR A SYSTEM HANDLING SMALL QUANTITIES OF LIQUID, AND AN ELEMENT MANUFACTURED BY THE METHOD

The present invention relates to a method for producing a heatable and refrigerable element for a system handling small quantities of liquid, said element being provided with flow channels and at least one liquid space communicating with said channels, and said element being functionally connected at a number of locations to a refrigerator and a heater.

FI patent publication 57850 proposes a procedure and an apparatus for handling small quantities of liquid, whereby the liquid is manipulated within a system consisting of spaces or chambers for holding or processing the liquid and channels interconnecting them, each of said channels being provided with at least one valve which is shut by refrigeration. Each valve is connected to a continuously operated refrigerator and provided with a separate electric heating element, so that when the heating element is active it keeps the temperature of the valve above the congealing point of the liquid in question, thus keeping the valve open, and when inactive, it lets the liquid in the valve be frozen, thereby shutting the valve. Thus, the manipulation of the liquid in the system, based on moving the liquid from one space to another by virtue of pressure differences, is achieved by electrically controlling the heating elements of the valves The apparatus presented in this publication is designed for use mainly as an automatic analyzer, in which the manipulation of the liquid is exclusively based on the pressure differences between the spaces and on electronic control of the heating elements, using no movable mechanical parts.

According to FI patent publication 57850, the refrigerable valves are formed by placing two blocks of material against each other in such manner that a valve is formed between the opposite surfaces One of these blocks contains the flow channels leading to the valves, while the other block, connected to the refrigerator, is provided with heating elements placed in the region of the valve (s) and used for opening and closing the valves To regulate the heating and cooling of the valves, the valve areas are provided with heat insulation, and valves placed side by side are isolated from each other by freezing a liquid in the gaps between the surfaces of the valve body pieces.

FI patent publication 70331 proposes an improved solution based on the aforementioned principle of forming a valve. The main feature of this solution is that the valves are formed by providing cut-outs on the surface of at least one of the oppositely placed blocks, and that the opposite surfaces of these blocks are coated with a thin layer of a chemically inert material which acts as a covering of the heating elements and heat insulation. In this solution, the valves can also be provided with inert stopping elements placed in said cut-outs to allow instantaneous shut-off of the liquid flow into the valve. According to the publication, this inert material consists in the first place of a fluoropolymer, such as teflon, although precious metals are mentioned as a possible alternative. In practical applications of the principle, a fluoropolymer has been used.

It has been found that the solution proposed in the aforementioned FI patent publication 70331 has the disadvantage that in the course of time water penetrates through the thin polymer layer, resulting in the formation of ice under the layer in the areas subject to refrigeration. In practical use, as the valve is alternately heated and refrigerated, the melting and re-freezing of this external layer of ice increases the thermal load, resulting in a slower and less accurate operation of the valve A similar effect also results from the fact that ice conducts heat considerably better than the polymer constituting the valve surface. Consequently, when the valve is being shut, the process of settlement of the boundary layer of the ice blockage is slow.

Furthermore, the valve construction proposed by said FI patent publication 70331 has other drawbacks not associated with the material used as coating of the bodies between which the valves are formed One of these drawbacks is the bulky construction, involving a large thermal mass and a low heating and refrigerating efficiency. Another disadvantage is found in the geometry of the valves and flow channels, which is due to the fact that the bodies limiting the valves are manufactured by casting into moulds, in which technique the casting has to be subsequently removed from the mould. As a result, the valves and channels show sharp angles and corners which, due to capillary forces, retain some liquid, which constitutes an impediment to the cleaning and fast drying of the channels This may result in dosage errors and contamination of the liquid.

The object of the present invention is to create a new technique for producing elements containing flow channels and one or more spaces or chambers for a liquid whereby the aforementioned drawbacks associated with the previously known techniques are eliminated. The method of the invention is characterized in that the element is produced by use of removable mould serving as a substrate for deposition, by depositing one or more metallic materials in such a way that deposited metal forms the shell of the element, by removing the mould, and by connecting the shell at said locations to a refrigerator and a heater the production being carried out so that the thermal conductivity of the structure as obtained at the locations where the shell of the element has been connected to a refrigerator and a heater substantially exceeds the thermal conductivity of the shell areas adjacent to said locations.

By applying the method of the invention, a metallic element with a very small thermal mass and a watertight shell is produced. These features allow an accurate and fast regulation of temperature. The definition stating that the thermal conductivity of the structure including the element and the connecting bridges to the heating and/or refrigerating means at the locations of the connections, substantially exceeds the thermal conductivity of the shell areas adjacent to said locations means in practice that the heat flux caused by a temperature difference through the locations referred to is preferably at least five times as high as the heat flux through the adjacent areas, and, depending on the case, may even be tenfold or higher. This is to say that a steep temperature gradient is formed between the locations which are connected to a refrigerator and a heater and the adjacent shell areas.

An essential advantage of the solution of the invention is that the mould used in forming the element can easily be shaped in accordance with the desired shapes of the flow channels and liquid spaces Thus, undesirable sharp angles and corners can be avoided, and, after deposition of the metal and removal of the mould, the result is an element whose flow channels can be flushed and dried quickly with a blast of air to ensure that no dosage errors will occur.

As taught by the present invention, refrigerable valves can be formed in the element by making the flow channel sufficiently narrow at least in one dimension at the relevant location and coupling this location to a heater and a refrigerator. In addition to or instead of this, the element can be provided with liquid spaces connected either directly or indirectly to a heater and a refrigerator to allow fast and accurate regulation of the temperature of the liquid in the spaces. In liquid analyzing equipment such spaces are used for mixing and incubation purposes An example of the possibilities of application of the solution of the invention is DNA processing in gene technology as proposed by U.S. Pat. No. 4,683,202, involving the incubation of a liquid sample in fast-changing temperatures to achieve certain reactions. According to this publication, the samples are processed inside a massive metal block in which the changes of temperature are much too slow in view of reliable completion of the reactions This disadvantage can be avoided by using an element manufactured as provided by the present invention. Moreover, the invention allows the automatization of the liquid handling processes, thus avoiding the contamination problems associated with manual procedures.

The deposition of metal may be carried out by way of electroformation in which the mould is arranged to serve as a cathode in a solution containing metallic ions. A layer of metal is deposited on the mould, and when required this layer may serve as a substrate for deposition of a further layer of the same or a different metal.

Alternative deposition techniques that may be used in the process of the invention include autocatalytic chemical reduction in which a metallic mould is submerged in a solution containing a compound of the metal to be deposited, e.g. a salt of said metal, and a reducing agent. The reaction, which may require heating of the solution, will cause deposition of a layer of reduced metal onto the mould, another technique which may be used is chemical vapor reduction which is rather similar but uses primarily organometallic compounds which are reducer in gas phase and deposited an a mould.

A further alternative for carrying out the deposition is sputtering in which a piece of metallic material and a metallic mould are placed in a vacuum chamber and a voltage of the magnitude of a thousand or more volts is connected between said piece and the mould. The voltage will ionize the metal and draw it onto the mould so that a layer is formed. The specific advantage of this method is that it may be used for deposition of any metal or alloy that might be required.

A still further alternative method for the deposition is evaporation of metallic material in a chamber in which the mould has been placed. The metal will deposit onto all available surfaces in the chamber including that of the mould. In ion plating evaporation is combined with above-mentioned sputtering, by which means a particularly fast deposition process is achieved.

In the method of the invention, the shell of the element can be produced in two phases by first depositing a first metal layer over the whole surface of the mould and then another layer on the first layer on the specific locations to be connected to the heating and refrigerating means. After the first deposition phase, the areas outside those locations can be covered with a protective coating, e.g. lacquer, to prevent the deposition of metal on these areas during the next phase.

For the successive deposition phases, it is preferable to select two metals differing in respect of thermal conductivity. In the first phase, a layer of the metal with the lower thermal conductivity value is deposited This metal may be e.g. nickel or an alloy containing nickel, such as kobaltous nickel having a cobalt content of a few percent, or a non-crystalline alloy consisting of nickel, cobalt and manganese, which alloy has a low thermal conductivity in comparison to other metals and is therefore especially suited for the purposes of the invention. However, there are other metals, e.g. pure cobalt, iron, chrome and the precious metals, that can be used in the first deposition phase. In the second phase, a metal with a better thermal conductivity is used. Of these, pure copper is the preferable choice, although e g. silver may also be used The thickness of the layer of metal, e.g. a nickel alloy, deposited in the first phase is preferably in the range 10–100 $\mu$m, while the layer of metal, preferably copper, deposited in the second phase is 10–500 $\mu$m thick. To achieve the desired difference in thermal conductivity or heat flux, the metal layer deposited in the second phase must generally be thicker than the layer deposited in the first phase. This is necessary especially when the same metal is used in both phases of deposition. In that case the result is an essentially homogenous element whose performance depends solely on the differences in the thickness of the shell at different locations.

As the shell of the element is produced in two phases it is possible to use in both phases the same deposition technique, e.g. electroformation. However, it is as well possible to use different techniques in the different phases, e.g. electroformation for the deposition of the first metal layer and sputtering for the deposition of the second layer. With regard to the different techniques referred to in the foregoing the only limitation is that evaporation is not suitable for the second phase as it is not possible to restrict deposition of metal to the specific unprotected locations only, in all other techniques including ion plating, the protective coating works by preventing deposition on the coated areas.

To enable the mould to be removed from inside the deposited layer of metal, the mould can be made of a dissoluble material, such as aluminium. Aluminium is suitable for all the different deposition techniques which have been described. In this case the solvent used of removing the mould may be e.g. a strong and hot solution of lye. The mould will dissolve more readily if it is partly or wholly tubular so that the dissolvent can be passed through it.

Alternatively, the mould may be made of a material whose melting point is low enough to allow the mould to be removed from inside the metal shell by smelting Such materials include certain metal alloys, e.g. alloys of tin, bismuth and lead, which have a melting point in the range of 69°– 200° C., as well as wax and plastic. Moulds made of the latter materials, however, have to be metal plated before they can serve as substrates for the deposition of the metal layers (except for deposition by evaporation).

In some cases it may even be possible to use a mould composed of several parts which can be pulled out separately from inside the metal shell after the deposition phases and used again The difference between this technique and the conventional metal mould process is the fact that the mould is made of separable parts, enabling it to be removed.

For the connection of the shell of the element at the desired location to a refrigerator, the method of the invention uses a bar-shaped or a plate-like bridge made of a material having a good thermal conductivity, e.g. copper. An essential consideration is that the bridge should have a small mass, so that it is capable of sufficiently fast operation. The heating of the shell can be implemented by providing the bridge connecting the refrigerator to the shell with a suitably insulated electric heating resistor. As soon as power is switched on, the heating effect of the resistor effectively eliminates the cooling effect of the refrigerator. In a preferable construction the bridge may consist e.g. of two layers of copper with an insulating layer of plastic between them, the resistor wire being contained within the plastic layer.

Alternatively, the shell of the element may be heated by irradiation. It is possible to use electrically controlled radiation sources transmitting e.g. laser beams, mounted at suitable locations outside the shell.

The bridge connecting the shell of the element to the refrigerator can be attached to the shell by electrolytically depositing a layer of easily melting material, such as indium, onto the shell and then smelting this layer so that the material will merge the end of the bridge with the shell. To smelt this material, an oven may be used, but alternatively it is possible to make use of the electric resistor incorporated in the bridge by connecting it to a supply of electricity and letting the current flow until the heat thus generated causes the material to melt. While melting, the material, at first spread as an even layer, recedes towards the line of contact between the bridge end and the shell, forming a collar swell which, when solidifying, effectively integrates the bridge with the shell.

To enable the processes inside the element to be monitored, it is possible, using the same technique as in the case of the bridges connecting the refrigerator to the shell, to attach temperature sensors having a low specific temperature onto the shell of the element as needed. These sensors can be merged with the shell by means of indium or a similar, easily melting material deposited on the shell, preferably simultaneously with the merging of said bridges The temperature sensors can continuously supply control information on the movements of the liquid in the system, on changes of temperature of the liquid or gas as well as the freezing and thawing of the liquid in the valves belonging to the system.

As stated before, an element manufactured by the method of the invention can be so designed that it has one or more heatable and refrigerable regions where the flow channel is at least in one dimension narrow enough to allow these regions to act as valves that can block the channel by freezing. These may be so-called high-power valves which are able to block the passage of a liquid flowing through the valve, or they may be normal valves which are so dimensioned that their refrigerating capacity is sufficient to freeze stationary liquid inside the valve. Especially the high-power valves are best produced by using a bar-shaped mould which has a form corresponding to that of the flow channel to be formed and is flattened in such manner that, after deposition of the metal layers and removal of the mould, the result is a metal element in which, in the region where the mould was flattened, the channel inside it is a narrow slot constituting a valve. The direction in which the bar-shaped mould is flattened and the corresponding narrow passage are preferably at an angle of about 20°-60° relative to the longitudinal direction of the mould and the flow channel formed by it. Such an oblique slot, which may additionally have a tapering form towards its outflow end, is most advantageous with regard to dynamic stopping of the liquid flow through the valve.

The present invention also relates to an element manufactured by the method described above and designed for use in a system manipulating small quantities of liquid, comprising flow channels and at least one liquid space communicating with them, said element being functionally connected at a number of locations to a refrigerator and a heater. The element of the invention is characterized in that it comprises a set of flow channels and one or more liquid spaces enclosed by an integral metal shell having essentially tubular sections, said shell being connected at a number of locations to a refrigerator and a heater, and that said locations together with the connections to a refrigerator and a heater are made up so that the thermal conductivity of the structure at these locations substantially exceeds the thermal conductivity of the adjacent shell areas.

In its simplest form an element according to the invention may comprise just one liquid space of chamber and two or more flow channels connected to said space, each channel being provided with at least one valve formed by a location in the channel connected to a refrigerator and a heater The valves thus enable an amount of liquid to be passed to the liquid space and closed therein by freezing the valves. However, to facilitate construction of larger liquid handling systems one element preferably contains larger amounts of liquid spaces and/or flow channels and valves, depending on the needs of the system in question.

The element of the invention may comprise one or more valves of the high-power type mentioned above that are capable of dynamically stopping the liquid flow, and, in addition to or instead of the high-power valves, one or more normal valves, also mentioned above, which can statically freeze the liquid present in the valve, and in addition to or instead of the valves one or more spaces or chambers in which the liquid is not congealed but which is still connected to a refrigerator and provided with at least one heater so as to enable the temperature of the liquid in the space to be regulated. In an analyzer handling small quantities of liquid, such a space can serve as a mixing or incubation chamber, where fast and accurate variation of the temperature of the liquid is required.

As an element made in accordance with the present invention has been tested. No leakage of water vapor through deposited metallic flow channels has been observed as an irregular or lengthening response time. The thermal leakage through the valves in resting state is surprisingly in the order of 1/10 W in this metallic structure, when it is one or more Watts in the polymer structure described in the FI patent 70331.

The typical opening and closing times of valves are tens to hundreds of milliseconds, in valves based on said previous patent typically seconds The apparent closing time for high-power valves as calculated from volume error made in stopping flow divided by flow rate typically gives 1/10 000s, with is more than ten times faster than with said previous patent and more than 100 times faster than a conventional solenoid valve, (if they could sense the incoming liquid). The improvement in quantitative performance of manipulating small liquid volumes is exemplified e.g. in dispensing 0.0625 ml liquid where the standard deviation of reproducibility was measured as 0.00001 ml, tens of times improvement over the said previous patent or over present conventional dispensing performance. In another test for an automatic dispensing of real small blood serum samples of 0.00022 ml the standard deviation was 0.0000007 ml including all other variations from a photometric measurement, a volume too small for the said previous patent.

A further benefit is the detection of an exact closing or opening time of each valve by detection the absorption or release of heat of fusion in each valve. Surprisingly, when an amount of 0.00002 ml of water based liquid freezes, that is the inside volume of a valve in the described system, the rate of cooling is so high, that the valve conduit cools below $-20°$ C., then upon sudden closing in less than 0.02 seconds its temperature jumps more than 5–10 degrees, which is each time clearly detected with said thermal sensing element Opening, absorbing the heat of fusion, is likewise easily detected thermally in each valve. An independent confirmation of valve opening and closing or liquid entering or leaving a channel or a space, can be obtained by applying and measuring responses to pressure differentials and looking for steady or changing pressure This conveniently takes place as an additional benefit while moving liquids with pressure differentials.

As to the preferred embodiments of the element of the invention, reference is made to the above description of the method of the invention and to the claims to follow.

In the following, the invention is described by the aid of examples with reference to the drawings attached, wherein:

FIG. 1 presents a partial view of a mould used in the forming of a heatable and refrigerable element as provided by the invention.

FIG. 9 represents a part of a finished element constructed as provided by the invention, in which the valves are coupled to a refrigerator by electrically heatable bridges.

FIG. 10 shows a section through an element in which a temperature sensor and an electrically heatable bridge leading to a refrigerator have been merged on the shell in the region of a valve.

FIG. 11 shows a similar section through another element constructed as provided by the invention.

Figure 1:
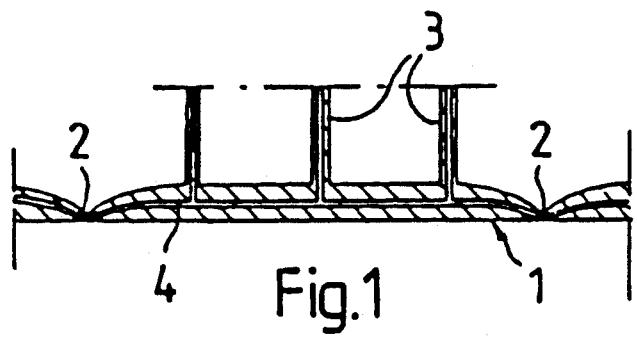
Figure 6:
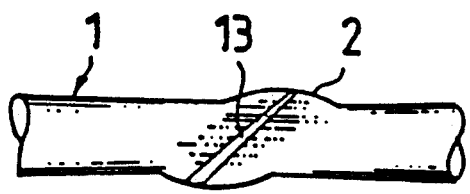
FIG. 6 shows a partial top view of a mould which has been flattened so as to produce a so-called high-power valve in the element to be formed.

FIG. 1 shows part of a fairly soft, easily deformable mould 1, made of aluminium. The mould has been flattened at two locations 2 in order to produce high-power valves in the element to be formed., These flattened portions are also represented by FIG. 6, which will be described in greater detail later on. Between the flattened parts 2 a space for a liquid is formed by means of the mould 1, which has three bar-shaped branches 3 between the flattened regions to form flow channels communicating with the liquid space in the element. The mould is entirely of a tubular construction, so that it can be later removed from inside the element by passing a flow of a dissolvent through the ducts 4 inside the mould.

Figure 2:
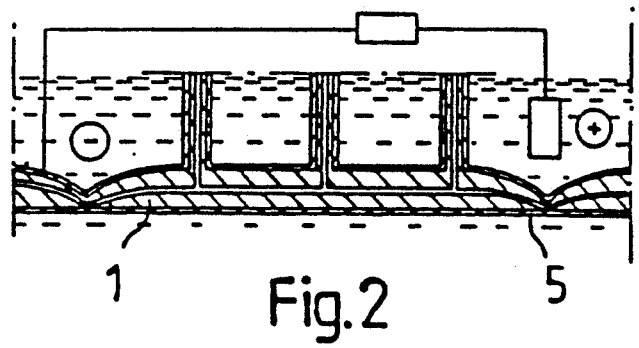
FIG. 2 represents the first phase of the electroforming of the shell of the element, during which a layer of metal is galvanically deposited on a mould.
Figure 3:
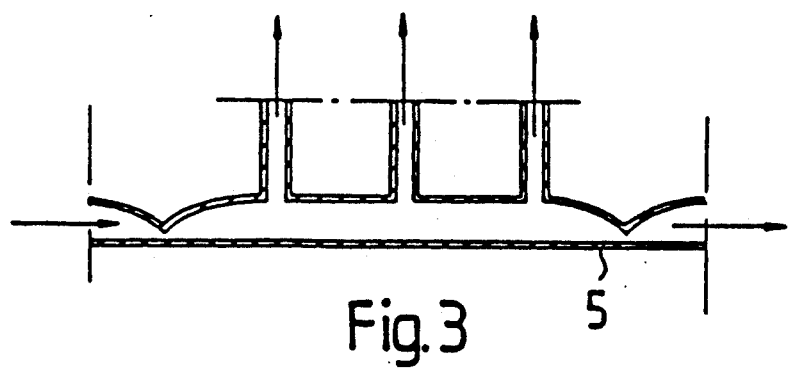
FIG. 3 represents the removal of the mould by dissolution from inside the shell thus obtained consisting of one layer of metal.

In the first deposition phase illustrated by FIG. 2 the mould 1 serves as a cathode in a sulphamate solution from which a layer of cobaltous nickel is deposited on the mould, the resulting layer having a thickness of 10–100 $\mu$m, preferably 30 $\mu$m, and a cobalt content a few per cent. This metal layer is identified by reference number 5 in FIG. 2. Upon completion of the deposition, the mould 1 is removed by supplying a hot, strong solution of NaOh into the ducts 4 inside it. The solution dissolves the aluminium mould but has no effect on the cobaltous nickel layer deposited on it. The result is a metal shell 5 of cobaltous nickel as shown in FIG. 3, the inside of which already has a shape corresponding to that of a finished element.

Figure 4:
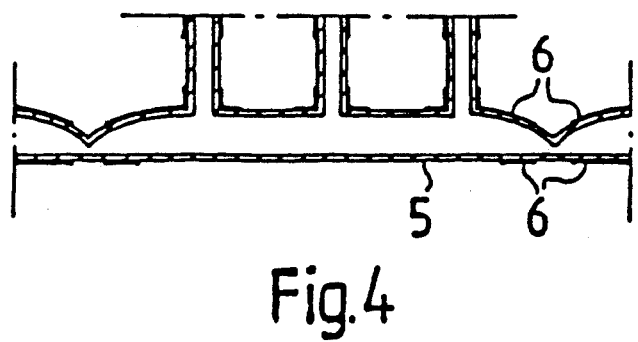
FIG. 4 represents the metal shell thus obtained, certain parts of which are provided with a protective coating.
Figure 5:
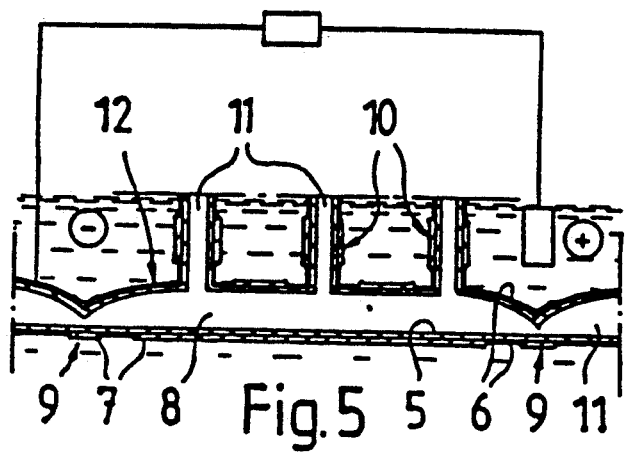
FIG. 5 represents the second phase of the electroforming of the shell in which a second layer of metal is galvanically deposited on the unprotected areas of the shell.

As a preliminary measure before the second deposition phase, certain parts of the outer surface of the cobaltous nickel shell 5 thus obtained is covered with a protective coat 6 of e.g. lacquer as shown in FIG. 4. The shell 5 is then immersed as shown if FIG. 5 as a cathode in a solution of copper sulphate containing sulphuric acid. A copper layer 7 is now deposited only on those areas of the shell which are not covered with lacquer 6. The thickness of the copper layer may vary in the range 10–500 $\mu$m. As copper and cobaltous nickel differ in respect of thermal conductivity, the areas of the shell provided with a copper layer 7 have a thermal conductivity about ten times as high as that of the areas consisting of cobaltous nickel only even when the two layers deposited are or equal thickness. The result of the second deposition phase is an element 12 consisting of a liquid space 8, valves 9 at either end of the space and three flow channels 11 communicating with the liquid space and provided with valves 10. The element is ready for connection to a refrigerator and heaters as explained below in connection with FIG. 9. If desired, the protective lacquer 6 can be removed from the surface of the element, though this is not necessary.

The above description in connection with FIGS. 2-5 refers to production of the element by electroformation. Alternatively the production may utilize non-electrolytic deposition techniques in which the metal is reduced chemically, catalysed by the metal (or alloy) itself. According to the invention an element can be made autocatalytically from nickel and phosphor by depositing on aluminum mandrels nickel from $NiSO_4$ or from $NiCl_2$ using $NaH_2PO_2$ as reducing agent at the temperature of 90°-92° C., whereby the amount of phosphor incorporated in the deposited nickel is controlled by adjusting the pH. The incorporated phosphor very beneficially reduces the thermal conductivity of deposit for the first deposition phase. An autocatalytically reduced layer of copper can be made similarly by using $CuSO_4$ and formaldehyde at the temperature of about +40° C.

The deposition of metal layers according to the autocatalytic chemical reduction techniques may be carried out generally as described in the above with reference to FIGS. 2-5, including removal of the mould and the protective coating preceding the second deposition phase. The essential difference is that no electric current is needed for accomplishing the deposition of the metals.

Figure 2A:
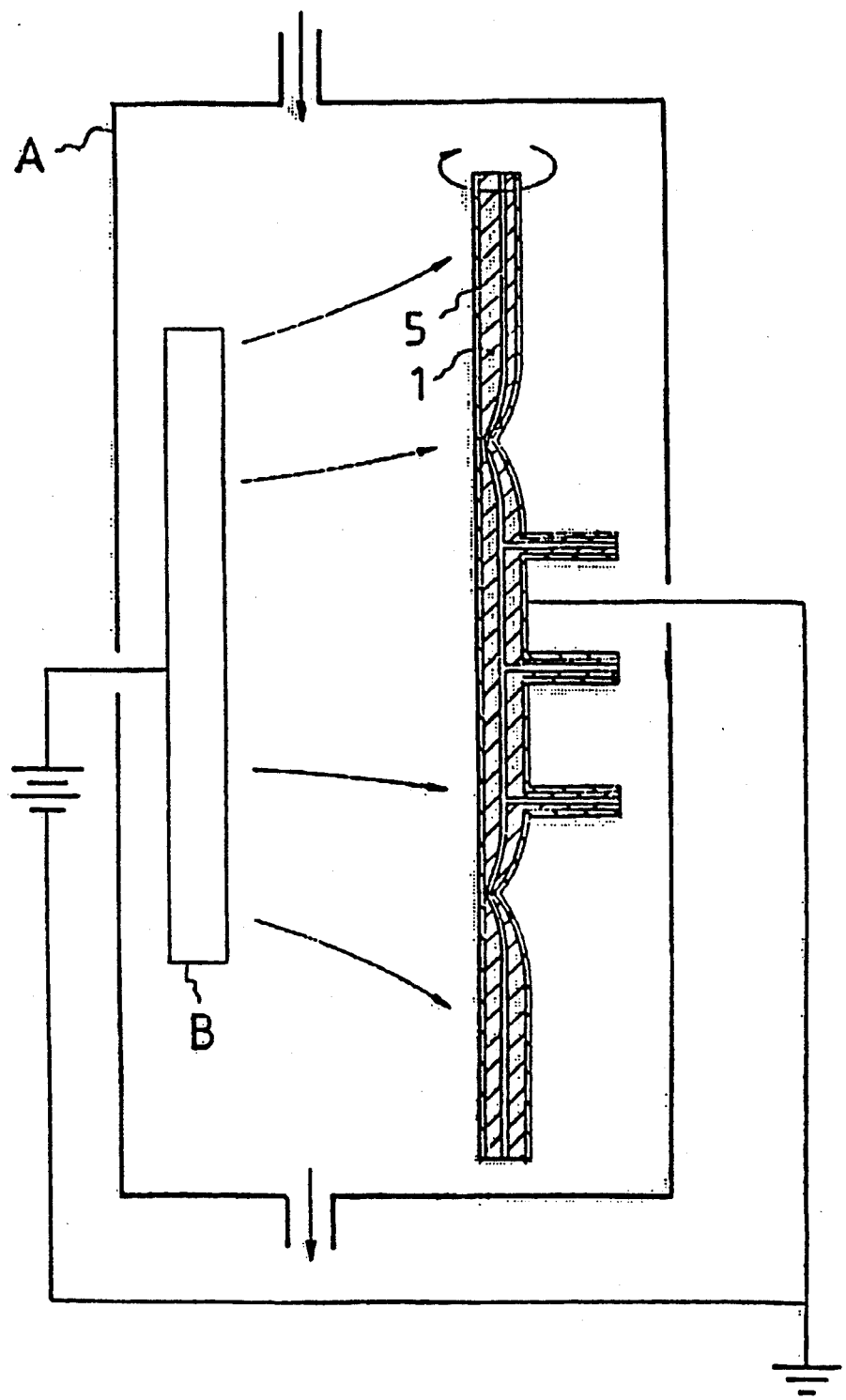
FIG. 2a represents the first phase in an alternative process for forming the shell of the element, in which a layer of metal is deposited on a mould by sputtering in a vacuum chamber.

FIG. 2a shows an alternative technique in which a layer of metal 5 is deposited onto a metallic mould 1, which may be of aluminium, by sputtering In partial vacuum of ionized argon gas in a gas discharge chamber 20 a there is connected a voltage of one thousand to few thousand volts DC or radiofrequency to a piece of the metal B to be deposited by sputtering, which is made cathode and the mould 1 is made anode. Although sputter deposition is considerably slower than previously explained deposition methods in liquid media, it has the great advantage of being able to deposit any metal or alloys a specific application requires.

A high vacuum is the environment for evaporation deposition of metals which is not very suitable due to too high temperature for moulds used in the present invention but its combination with sputtering results a deposition process known as ion plating which takes place in a suitable temperature and can have even higher speeds than in liquid deposition processes.

Figure 7:
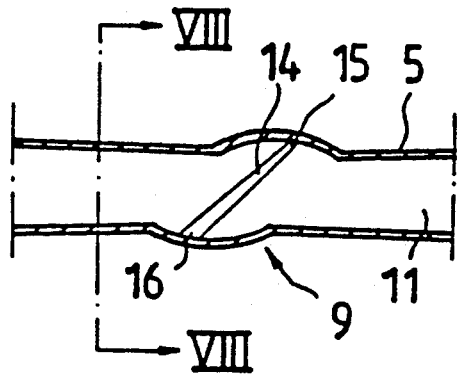
FIG. 7 represents the region of a valve after deposition of the first layer of the shell and removal of the mould.
Figure 8:
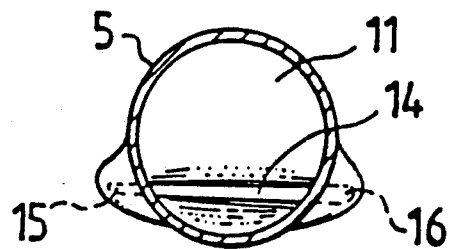
FIG. 8 shows a section VIII—VIII through the valve in FIG. 7.

The form of the valves 9 at the ends of the liquid space 8 is illustrated by FIGS. 7 and 8. From FIG. 6, representing the region of the mould 1 where a valve 9 is formed, it can be seen that the bar-shaped mould has been flattened in a direction which is at an angle of about 45° to the longitudinal direction of the mould. The flattened portion of the mould is identified by reference number 13 in the figure. From FIGS. 7 and 8 it can be seen that the cobaltous nickel shell 5 obtained after removal of the mould has a narrow slot 14, likewise at an angle of about 45° to the longitudinal direction of the flow channel 11 inside the shell, in the region of the flattened part of the mould. As shown, the slot or choke 14 tapers towards one end 15 in the direction of the liquid flow in the channel 11. The slot 14 may have a width in the range of approx. 200-30 μm at the inflow end 16 and approx. 30-2 μm at the outflow end 15. Such a design of the choke 14 ensures that the flow of liquid arriving into the valve consisting of the choke 14, which is connected to a refrigerator as explained below, will not flow straight through the slot 14 at its wider influx end 16 but, by virtue of capillary forces, will instead flow along the slot towards its narrower efflux end 15, so that the delay involved is sufficient to allow the liquid in the choke 14 to be frozen so as to close the valve.

FIG. 9 represents an element 12 produced as illustrated by FIGS. 1-5. The regions of the valves 9,10 are connected to a refrigerator by means of plate-like bridges 17, which are provided with electrical resistors 18 in such manner that the bridges also act as heaters. In the embodiment shown in the figure, the bridges 17 are pointed tongues of a single plate-like body 19, the tongue tips, which are suitably bent if necessary, being attached to the copper layers covering the regions of the valves 9,10. The bridges 17 are preferably composed of a double copper film, the resistor wires 18 being contained within a layer of plastic 21 (cf. FIGS. 10 and 11) between the copper films 20.

FIG. 10 illustrates the way in which the end of the bridge 17 is attached to the copper layer 7 on the shell of the element 12. A thin layer 22 of indium is deposited onto the copper layer 7 and then smelted so that it binds the bridge 17 and the copper layer 7 together. The joint is secured by a drop-like formation 23 of indium gathered by the agency of capillary forces around the tip of the bridge 17 during the smelting.

As shown in FIG. 10, a temperature sensor 24 is connected to the copper layer 7 on the side of the valve 10 opposite to the bridge 17. The sensor 24 consists of a thermoelement, the ends of whose leads are merged with the copper 7 in the same manner as the tip of the bridge 17. The thermoelement 24 makes it possible to monitor the operational state of the valve and the changes of state of the liquid in it.

FIG. 11 largely corresponds to FIG. 10 except that it shows an entire bridge 17 connected to a continuous-action refrigerator 25. In addition, in the element shown in this figure the copper layer 7 surrounding the large liquid space 8, which may serve e.g. as a dosage space in an analyzer, is connected via a copper bridge 26 to the copper layer 7 surrounding the flow channel 11 leading to the space, said bridge 26 serving to maintain an equal temperature in these parts of the element. The figure shows an ice blockage 27 closing the valve 10 in the channel 11. It should be noted that the valve 10 shown in FIGS. 10 and 11 is a so-called normal valve, in which stationary liquid is congealed by the action of the refrigerator 25 via the bridge 27 when the heating resistor is inactive. However, in the case of the high-power valves 9 represented by FIGS. 7 and 8, which are capable of dynamically stopping the liquid flow, the copper layer 7 surrounding the valve is connected in the same way via a heatable bridge 17 to a refrigerator 25.

Depending on the use for which the element is designed, it may be necessary to use a chemically inert precious metal to form the internal surfaces of the flow channels 11 and possible liquid spaces 8 of the element In this case the manufacturing process described above can be modified e.g. by first depositing a nickel layer of a few μm onto the mould 1 and then a layer of a precious metal, e.g. gold, of about equal thickness onto the nickel layer Next, a metal shell layer 5, e.g. of cobaltous nickel as explained above, is deposited on the precious metal in the manner illustrated by FIG. 2. The subsequent removal of the mould 1 can be effected using a strong solution of hydrochloric acid, which dissolves both the aluminium mould and the first nickel layer deposited on it, so that the layer of precious metal will constitute the internal surface of the element After this, the manufacturing process is continued in the manner described above.

The proposed element 12 is designed for use as a component in a system which manipulates or processes small quantities of liquid, especially in ah automatic analyzer operated under electronic control. Thus the element, suitably connected to other elements manufactured in essentially the same way, may constitute part of a large assembly of equipment. However, even a simple element consisting of a liquid space communicating with a few flow channels provided with valves may suffice as an instrument for carrying out certain operations with small quantities of liquid.

It is obvious to a person skilled in the art that different embodiments of the invention are not restricted to the examples described above, but that they may instead be varied within the scope of the following claims. For instance, in an element constructed as illustrated by FIG. 11, the liquid space 8 could be directly connected to a refrigerator 25 by means of the same kind of bridge 17 provided with a heating resistor 18 as is used for connecting the valve 10. In this case the temperature in the space could be regulated so as to allow the space to serve as an incubation chamber, and the end of the bridge 17 could be attached to the copper layer 7 surrounding the liquid space 8 with the aid of indium as explained in connection with FIG. 10. It is also possible to replace the thermoelement serving as a temperature sensor with some other type of sensor, e.g. a thermistor, having a sufficiently low thermal capacity. Further, the heating resistor 18 incorporated in the bridge 17 can be made of a suitable material, such as nickel, that enables the resistor to act as a temperature sensor.

I claim:

1. A method for making an element that controls the flow of small amounts of liquid, said element having an inside liquid space and flow channels extending from said space, the method comprising the steps of:
   providing a mould having an external shape that corresponds to the inside shape of said element;
   depositing metallic materials having predetermined thermal conductivities over all exterior surfaces of the mould to form a shell having a plurality of locations wherein said shell has a predetermined high thermal conductivity and the areas of said shell that are adjacent to said locations are of a predetermined lower thermal conductivity;
   extracting said mould from said shell so that said shell defines a liquid space and a plurality of flow channels extending from said liquid space; and
   connecting said locations of said shell to a refrigerator and a heater to enable controlled cooling and heating of a liquid within said element at said locations.

2. The method according to claim 1 wherein the step of depositing comprises electrolytically depositing said metallic materials onto said mould.

3. The method according to claim 1 wherein the step of depositing comprises:
   immersing said mould in a solution of oxidized metallic materials;
   chemically reducing said oxidized metallic materials to form said metallic materials whereby said metallic materials deposit onto said mould.

4. The method according to claim 1 wherein the step of depositing comprises:
   exposing said mould to a gaseous phase of oxidized metallic materials;
   chemically reducing said oxidized metallic materials to form said metallic materials whereby said metallic materials deposit onto said mould from said gaseous phase.

5. The method according to claim 1 wherein the step of depositing comprises:
   placing said metallic material and said mould in a partially evacuated chamber;
   connecting said metallic material and said mould to a source of electrical power and applying an electrical voltage to cause said metallic material to ionize and deposit onto said mould.

6. The method according to claim 1 wherein the step of depositing utilizes evaporation techniques, in which metal deposits on a mould placed in said chamber.

7. The method according to claim 1 wherein the step of depositing is carried out in two steps comprising:
   depositing in a first deposition step a first metal layer having a first thermal conductivity over the whole surface of the mould; and
   depositing in a second deposition step a second metal layer having a second thermal conductivity higher than said first thermal conductivity on said first metal layer wherein said second metal layer is deposited only at said plurality of locations to be connected to a heater and a refrigerator.

8. The method according to claim 7 further including the step of covering areas of said first metal layer that are outside said plurality of locations with a protective coating after said first deposition step, thereby preventing said second metal layer from being deposited on those areas covered with said protective coating.

9. The method according to claims 7 or 8 wherein a substantially thicker layer of metal is deposited by said second deposition step than by said first deposition step.

10. The method according to claim 7 wherein said first metal layer is nickel and said second metal layer is copper.

11. The method according to claim 7 wherein said mould is extracted from said shell after said first deposition step.

12. The method according to claim 1 wherein said mould is at least partially tubular in construction and the step of extracting comprises passing through said mould a solvent capable of dissolving said mould.

13. The method according to claim 12 wherein said mould is made of aluminum and said solvent comprises a solution of lye.

14. The method according to claim 1 wherein said shell is connected to said refrigerator by a bridge made of a material having a thermal conductivity that exceeds the thermal conductivity of said areas of said shell that are adjacent to said locations.

15. The method according to claim 14 wherein said bridge includes an insulated electric resistor so that said bridge also acts as a heater when an electric current is passed through said resistor.

16. The method according to claims 14 or 15 wherein said bridge is connected to said shell by the steps comprising:
   contacting said shell with a first end of said bridge to form a contact point;
   depositing an easily melted material onto said shell and onto said first end of said bridge at said contact point wherein said easily melted material has a melting point lower than said metallic materials; and
   smelting said easily melted material so that it merges said first end of said bridge together with said shell at said contact point.

17. The method according to claim 16 wherein said easily melted material is indium.

18. The method according to claim 1 wherein said locations are, at least in one dimension, sufficiently narrow to allow a liquid inside said flow channels at said locations to be frozen by said refrigerator, said locations thereby acting as valves that control the flow of said liquid through said flow channels.

19. The method according to claim 18 wherein said valves are produced by flattening said mould in such manner that, after the steps of depositing said metallic materials on said mould and extracting said mould, a narrow slot is produced in said flow channels inside the metal shell at said locations where said mould was flattened.

20. The method according to claim 19, wherein said mould has a longitudinal axis and is flattened in a direction which is at an angle of from about 20° to about 60° relative to said longitudinal axis of said mould.

21. A method for making a device for controlling the flow of small amounts of liquid, the method comprising the steps of:
provididing a hollow mould having an elongate central body portion, a first flattened portion adjacent one end of said body portion and a second flattened portion adjacent the opposite end of said body portion, said mould further including a plurality of branches extending from said central body portion between said first and second flattened portions;
depositing a first metal having a first thermal conductivity over all exterior surfaces of said mould to form a shell;
extracting said mould from said shell so that said shell defines a liquid chamber formed about said central body portion, a pair of constricted inlets formed about said first and second flattened portions, and a plurality of liquid flow channels formed about said branches and positioned between said constricted inlets; and
attaching a refrigerating and heating element to said shell adjacent each of said constricted inlets whereby liquid in or flowing through said pair of constricted inlets may be frozen by activating said refrigerating element.

22. The method according to claim 21 further comprising depositing a second metal on said first metal only at said first and second flattened portions, wherein said second metal has a thermal conductivity that exceeds said first thermal conductivity.

23. The method according to claim 21 wherein said mould is made of a third metal and the step of depositing comprises:
immersing said mould in a solution that contains ions of said first metal;
connecting said mould to a source of electricity so that said mould acts as a cathode;
inserting an anode into said solution; and
passing a current of electricity through said solution to deposit said first metal onto said mould.

24. An element for use in a system that controls the flow of small quantities of liquid, said element comprising an integral metal shell that defines at least one liquid space having a first end and a second end and a plurality of flow channels that extend from said liquid space between said first and second ends, said shell being connected to a refrigerator and a heater at a plurality of locations wherein said shell has a thermal conductivity that is substantially greater than the thermal conductivity of areas of said shell adjacent said locations.

25. The element according to claim 24 wherein the thickness of said shell at said locations substantially exceeds the thickness of said shell in said areas adjacent to said locations.

26. The element according to claims 24 or 25 wherein said element comprises:
a shell formed from a first metal wherein said first metal extends over the whole area of said element, said first metal having a first thermal conductivity; and
a second metal at said locations of said shell that are connected to a refrigerator and a heater, said second metal having a thermal conductivity that exceeds said first thermal conductivity.

27. The element according to claim 24 wherein said first metal is nickel or a nickel alloy, and said second metal is copper.

28. The element according to claim 24 wherein said shell is connected to said refrigerator by means of a bridge made of a material that has a thermal conductivity that exceeds said thermal conductivity of said areas adjacent to said locations.

29. The element according to claim 28 wherein said bridge is a copper bridge.

30. The element according to claim 28 wherein said bridge includes an insulated electric resistor so that said bridge also acts as a heater when an electric current is passed through said resistor.

31. The element according to claims 28 or 30 wherein said bridge is attached to said shell with an easily melted material, said easily melted material having a melting point that is lower than the melting points of said bridge and said shell.

32. The element according to claim 31 wherein said easily melted material is indium.

33. The element according to claim 24 wherein said plurality of locations of said shell are, at least in one dimension, sufficiently narrow to allow a liquid in said flow channels at said locations to be frozen by said refrigerator, said locations thereby acting as valves to control the flow of said liquid through said flow channels.

34. The element according to claim 33 wherein said valve consists of a slot in said flow channels, said flow channels having a longitudinal axis, said slot being oriented at an angle of from about 20° to about 60° relative to said longitudinal axis of said channels.

35. The element according to claims 33 or 34 wherein said valve includes a temperature sensor.

36. The element according to claim 34 wherein said element comprises at least one mixing or incubation space that is connected to a refrigerator and includes at least one heater to regulate the temperature of a liquid in said space.

37. A device for controlling the flow of small quantities of liquids comprising:
a metal shell defining an elongate liquid chamber having first and second ends, a constricted first inlet adjacent said first end of said liquid chamber and a constricted second inlet adjacent said second end of said liquid chamber, said shell including a plurality of tubular flow channels extending from said shell between said first and second ends; and
a refrigerating element connected to said shell adjacent said first and second constricted inlets whereby liquid in or flowing through said constricted inlets may be frozen by activating said refrigerating element.

38. The device according to claim 37 wherein said shell comprises a first metal layer extending over the whole area of the device, and a second metal layer only at regions of said device that are to be connected to said refrigerating element, wherein said second metal layer has a higher thermal conductivity than said first metal layer.

39. The device according to claim 37 wherein the thickness of said shell at the locations where said shell is connected to said refrigerating element substantially exceeds the thickness of said shell in the adjacent areas of said shell.

* * * * *

UNITED STATES PATENT AND TRADEMARK OFFICE
CERTIFICATE OF CORRECTION

PATENT NO. : 5,311,896  
DATED : May 17, 1994  
INVENTOR(S) : Niilo Kaartinen

It is certified that error appears in the above-indentified patent and that said Letters Patent is hereby corrected as shown below:

Column 2, line 8  
"valve A" should read --valve. A--.  
Column 2, line 27  
"channels This" should read --channels. This--.  
Column 3, line 22  
"reactions This" should read --reactions. This--.  
Column 5, line 46  
"bridges The" should read --bridges. The--.  
Column 6, line 31  
"heater The" should read --heater. The--.  
Column 6, line 63  
"seconds The" should read --seconds. The--.  
Column 7, line 22  
"element Opening" should read --element. Opening--.  
Column 7, line 28  
"pressure This" should read --pressure. This--.  
Column 7, line 50  
"obtained consisting" should read --obtained, consisting--.  
Column 8, line 12  
"formed.," should read --formed.--.  
Column 9, line 19  
"sputtering In" should read --sputtering. In--.  
Column 9, line 24  
"sputtering,." should read --sputtering,--.

UNITED STATES PATENT AND TRADEMARK OFFICE
CERTIFICATE OF CORRECTION

PATENT NO.   : 5,311,896
DATED        : May 17, 1994
INVENTOR(S)  : Niilo Kaartinen It is certified that error appears in the above-indentified patent and that said Letters Patent is hereby corrected as shown below:

Column 10, line 57 "element After" should read --element.  After--.

Signed and Sealed this

Sixth Day of December, 1994

Attest:

BRUCE LEHMAN

*Attesting Officer*        *Commissioner of Patents and Trademarks*